(12) United States Patent
Blondeau

(10) Patent No.: US 7,153,275 B2
(45) Date of Patent: Dec. 26, 2006

(54) DEVICE FOR TAKING A SAMPLE FROM A BODY

(75) Inventor: Jérôme Blondeau, Clamart (FR)

(73) Assignee: Porges, Le Plessis Robinson (FR)

( * ) Notice: Subject to any disclaimer, the term of this patent is extended or adjusted under 35 U.S.C. 154(b) by 405 days.

(21) Appl. No.: 10/669,432

(22) Filed: Sep. 25, 2003

(65) Prior Publication Data

US 2004/0068231 A1  Apr. 8, 2004

(30) Foreign Application Priority Data

Oct. 3, 2002 (FR) .................................. 02 12234

(51) Int. Cl.
*A61B 10/00* (2006.01)
*A61B 17/32* (2006.01)
*A61B 17/14* (2006.01)

(52) U.S. Cl. ...................... 600/567; 600/562; 600/564; 606/167; 606/184

(58) Field of Classification Search ................ 600/562, 600/564, 567; 606/167, 184
See application file for complete search history.

(56) References Cited

U.S. PATENT DOCUMENTS

| 4,699,154 | A | | 10/1987 | Lindgren |
| 4,958,625 | A | | 9/1990 | Bates et al. |
| 5,842,999 | A | | 12/1998 | Pruitt et al. |
| 5,951,489 | A | * | 9/1999 | Bauer .......................... 600/567 |
| 5,989,197 | A | * | 11/1999 | Avaltroni ..................... 600/567 |
| 2004/0097830 | A1 | * | 5/2004 | Cooke et al. ................ 600/564 |

FOREIGN PATENT DOCUMENTS

| EP | 0238461 | 9/1987 |
| EP | 0435986 | 7/1991 |

\* cited by examiner

*Primary Examiner*—Max F. Hindenburg
*Assistant Examiner*—Jeffrey G. Hoekstra
(74) *Attorney, Agent, or Firm*—Stevens, Davis, Miller & Mosher, LLP

(57) ABSTRACT

A device for taking a sample from a body may include a needle and a cannula for taking a sample, slides connected to springs for priming the needle and the cannula, a control button for bringing the slides to a rearward position against the force of springs so as to prime the needle and the cannula, and a trigger mechanism. The slides may have limit stops that are transversely offset with respect to one another. The control button includes a lug that can be moved transversely under the action of a displacement device and acts sequentially on the offset limit stops so as to bring the slides one after the other to the rearward position.

11 Claims, 8 Drawing Sheets

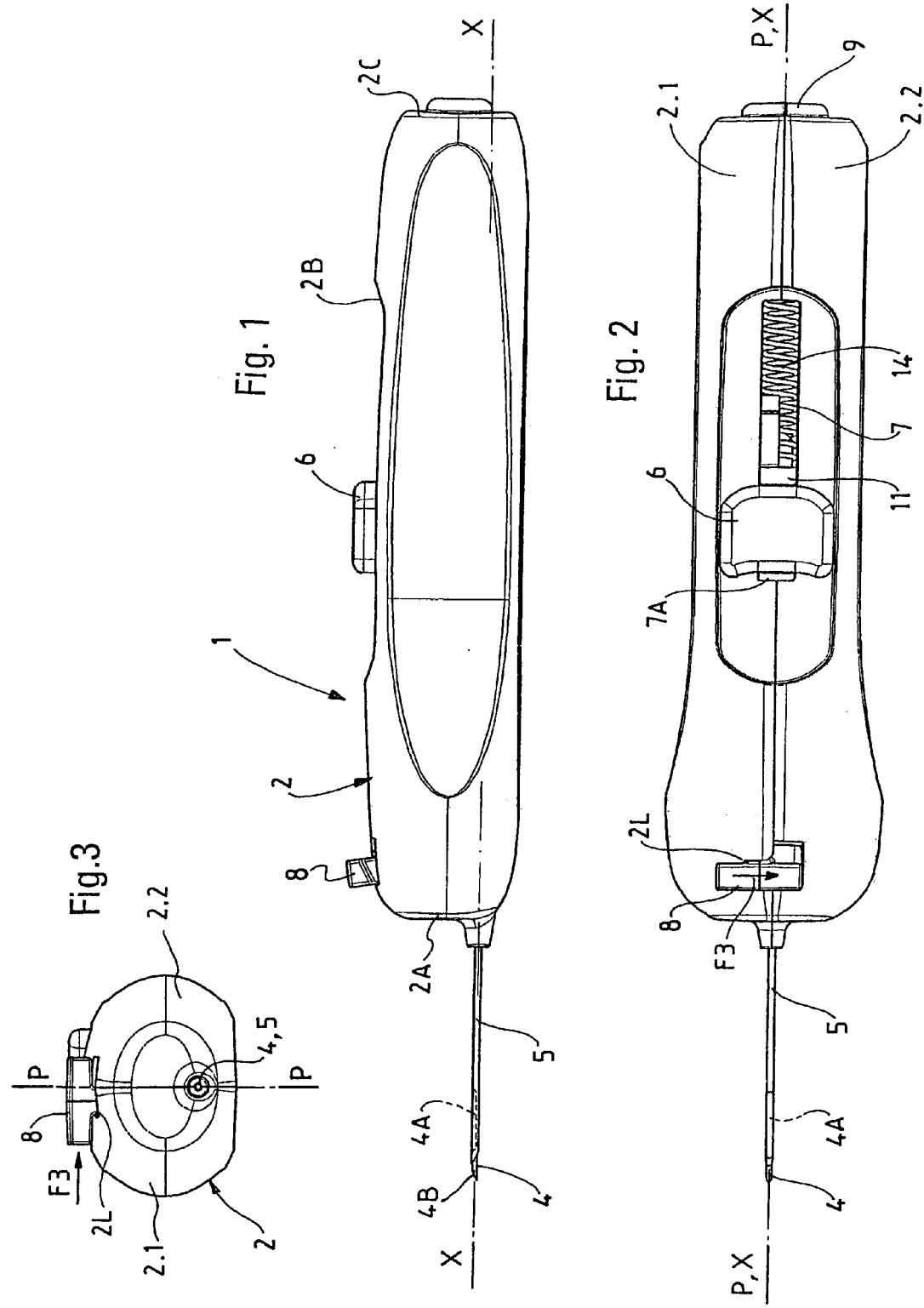

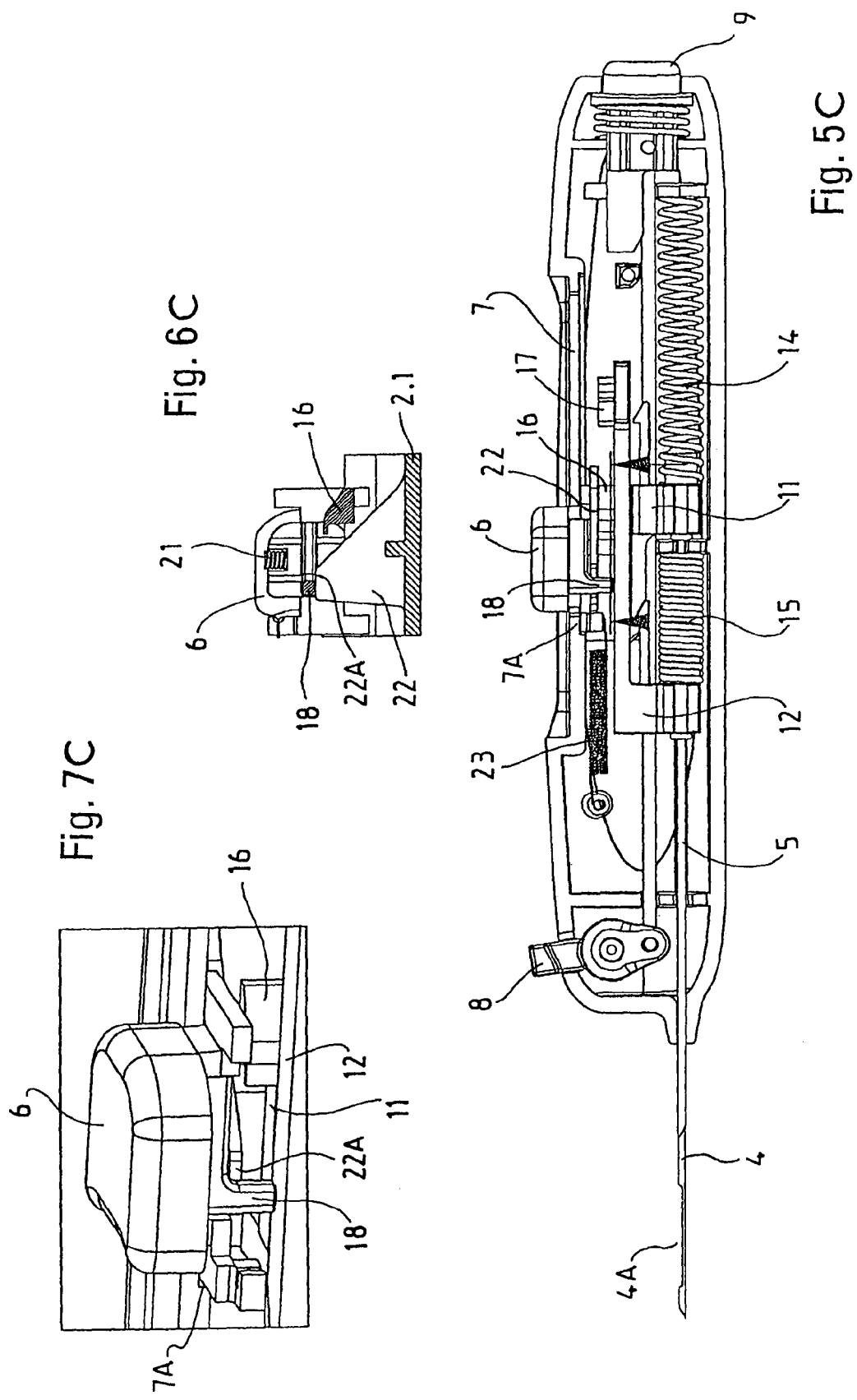

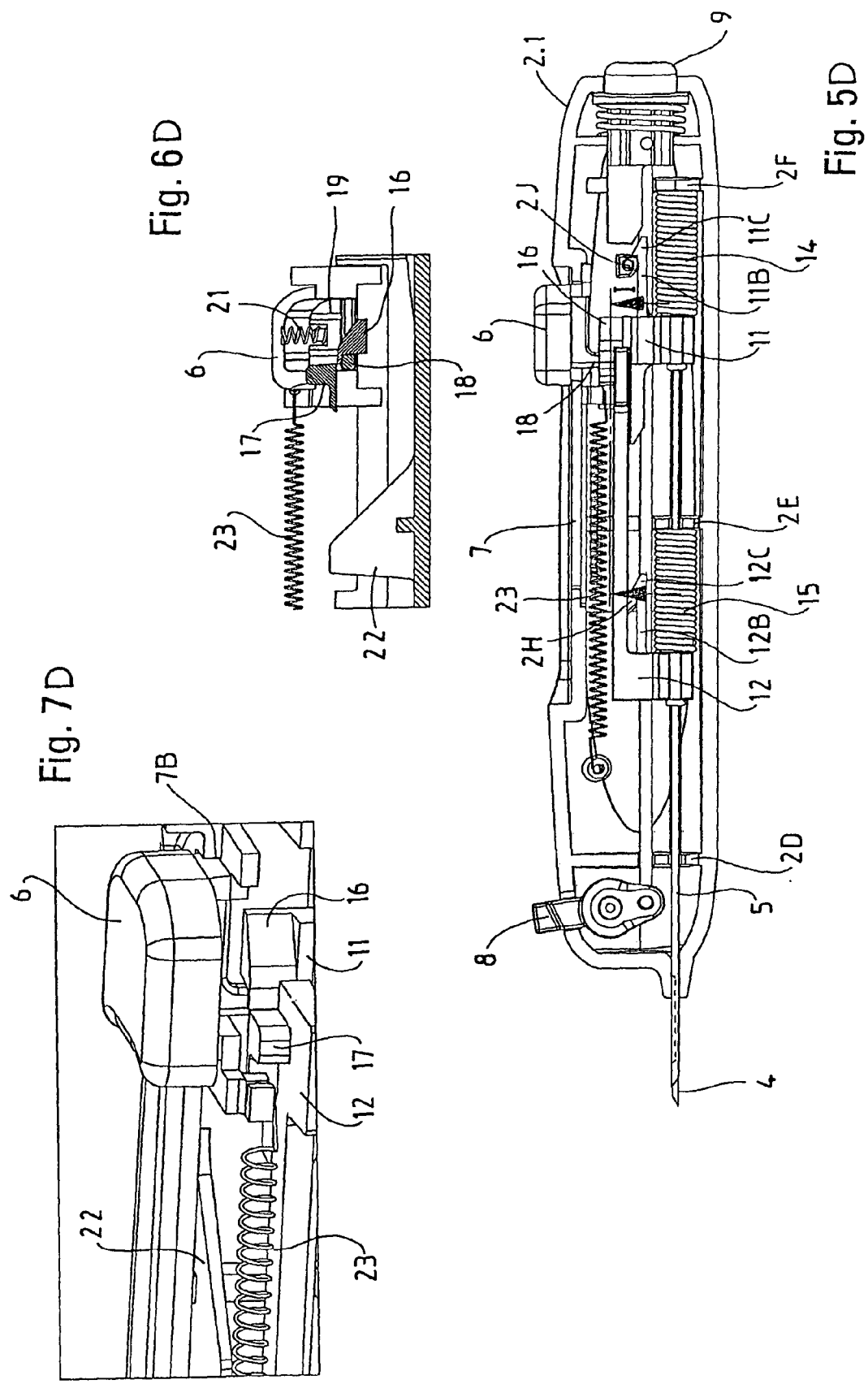

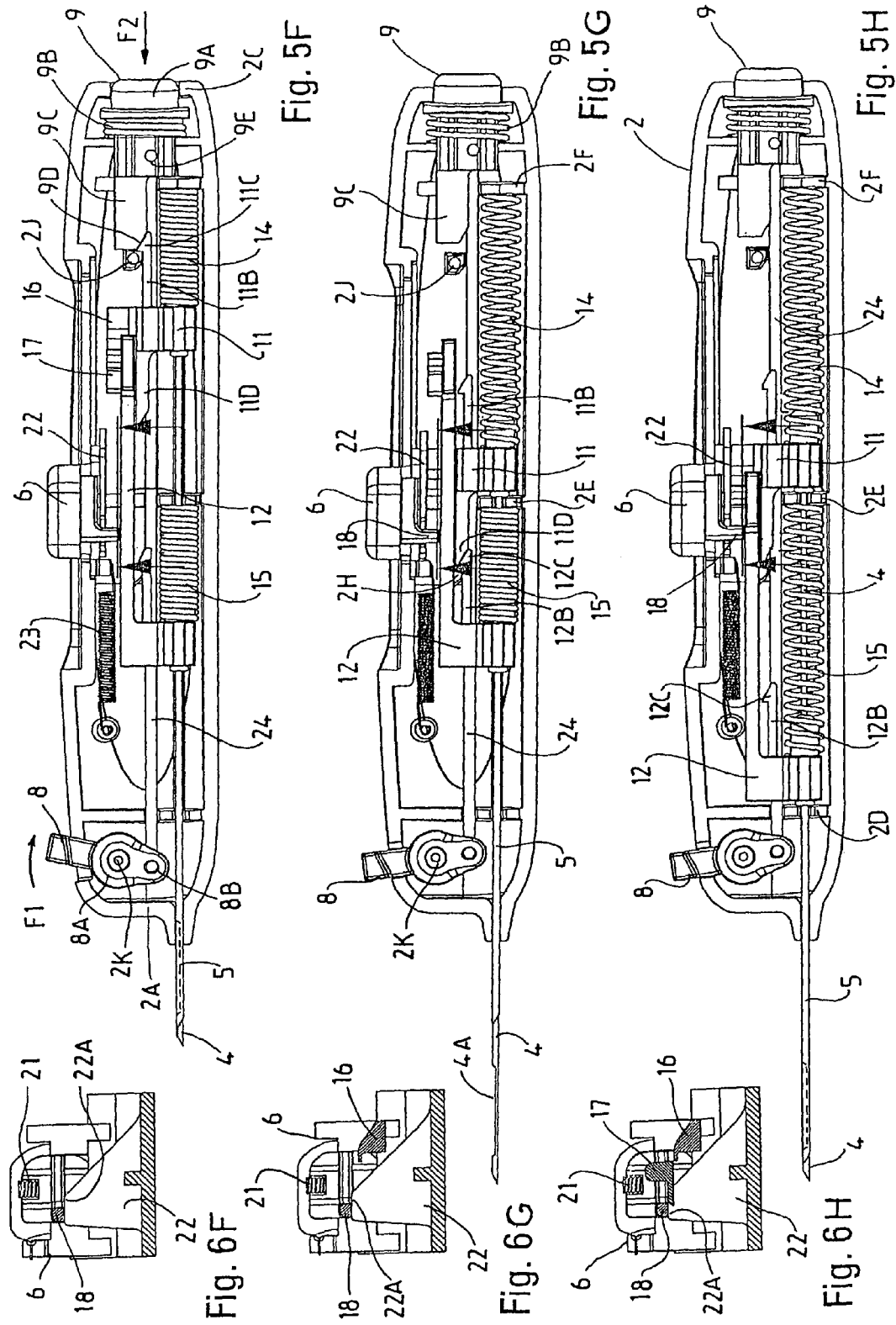

DEVICE FOR TAKING A SAMPLE FROM A BODY

FIELD OF THE INVENTION

The present invention relates to a device for taking a sample of tissue or of an organ from the body of a human or animal for examination purposes.

BACKGROUND OF THE RELATED ART

The taking of samples, generally referred to by the term biopsy, has become an increasingly frequent medical procedure since it permits, inter alia, operations for diagnosing pathological conditions following various examinations of the sample taken and makes it possible to reach, without causing injury, deep-lying organs such as the liver and kidneys.

Numerous sampling devices have therefore been developed to respond to demand, the aim being to facilitate their use by practitioners and to guarantee very reliable functioning.

Numerous devices for taking samples from the body are already known and these generally comprise:
  a needle whose distal end forms a recess able to receive said sample;
  a cannula coaxially surrounding said needle, said needle and cannula being able to slide relative to one another;
  slides connected respectively to said needle and cannula;
  springs connected respectively to said slides;
  a grippable housing of elongate shape, defining an inner seat inside which are arranged in series, on a longitudinal axis of said housing, said slides which are able to slide between a forward position in the housing, for which said needle and cannula are in a rest position and ready to be primed for taking a sample, and a rearward position for which said needle and cannula are in a primed, retracted position ready for said sampling;
  a control button for bringing said slides to the rearward position counter to said respective springs;
  means for blocking said slides in the rearward position; and
  a trigger mechanism for canceling said blocking means and, under the action of said springs, causing the forward displacement of said slides and firing of said needle and cannula.

Such devices are disclosed in, for example, European patents EP-0 238 461 and EP-0 435 986.

These devices described require the practitioner to use both hands to simultaneously charge the slides comprising needle and cannula, counter to the action of springs, which is not always easy to do.

SUMMARY OF THE INVENTION

The object of the invention is to make available a sampling device whose design is structurally simple and in particular allows the practitioner to bring said needle and cannula to the primed position using just one hand.

To this end, according to the invention, the sampling device of the type described above is distinguished by the fact that said slides comprise limit stops which are transversely offset with respect to one another, and said control button comprises a lug which can be moved transversely under the action of displacement means and acts sequentially on said offset limit stops in order to bring said slides one after the other to the rearward position.

Thus, by virtue of the invention, a single control button permits sequential charging of the needle and of the cannula, which is done in two separate movements: a first movement of translation of the button from an initial position, which for example brings the slide with cannula to the primed position, and, after return of said button to the initial position, a second movement of translation which brings the slide with needle to the primed position.

Using the device is straightforward and easy since the practitioner can prime it using just the thumb of one hand.

For example, said displacement means can comprise a spring arranged transversely between said button and said lug and permitting the latter to pass from a retracted position, for which one of said slides is displaced to the rearward position via its limit stop, to a deployed position for which the other slide is displaced to the rearward position via its offset limit stop, and an inclined ramp which is provided inside said housing and which returns said lug from its deployed position to its retracted position, upon return of said button to the initial position.

Said inclined ramp advantageously terminates in a lateral end edge on which, in the initial position of said button, said lug bears, compressing its spring, and which is situated at the same level as the limit stop of the slide to be displaced first. Thus, the lug is maintained in the retracted position and engages the limit stop of the corresponding slide as soon as the control button is displaced. The lug is connected to said button by, for example, a slideway connection and can slide transversely, via the latter, under the action of the displacement means.

In particular, said slide with cannula and its spring are situated at the front of said housing and are brought first to a rearward, primed position via said lug, while said slide with needle and its spring are situated coaxially at the rear of said housing and are displaced second to the rearward, primed position, the displacement of said slides and springs being limited by brackets fixed to said housing.

Said control button is preferably mounted so as to slide longitudinally through an oblong opening of said housing, and a spring arranged longitudinally connects said housing to said button in order to return the latter spontaneously to its initial position, against the corresponding front edge of said opening.

In a preferred embodiment, said blocking means comprise at least one bracket with elastically deformable hook issuing from each slide, and a corresponding fixed limit stop which is provided inside said housing and on which the hooked bracket of the corresponding slide engages when said slide arrives at the rearward position.

As regards said mechanism for triggering said sampling, it advantageously comprises, on said housing, a front tumbler and a rear tumbler which can be actuated independently of one another and act on said blocking means. The practitioner can use one or other of said tumblers to fire the sampling device. Said front and rear tumblers are preferably connected mechanically to one another by a connection rod situated inside said housing.

In a preferred embodiment, said rear tumbler comprises a pushbutton with return spring and equipped with a bracket arranged projecting into said housing in order to free said blocking means of said slide with needle, and said slide with needle is equipped moreover with a bracket arranged projecting in order to act on said blocking means of said slide with cannula, following its displacement to the forward position. Thus, ejection of the slide with needle takes place first, then that of the slide with cannula, making it possible to collect the body sample between the successive displacements of the slides to the forward position.

As regards said front tumbler, it can comprise a lever pivoting about an axis of said housing orthogonal to its longitudinal axis, said connection rod connecting said lever of the front tumbler to said pushbutton of the rear tumbler. The device advantageously comprises a safety means for rendering said trigger mechanism inoperative. For example, said safety means consists of a notch which is formed in said housing and in which said front tumbler can be received following a transverse displacement. The trigger mechanism is thus immobilized.

Moreover, said housing is preferably made up of two half-shells joined together along the longitudinal plane.

BRIEF DESCRIPTION OF THE DRAWINGS

From the figures in the attached drawing, it will be readily appreciated how the invention can be realized. In these figures, identical references designate similar elements.

FIGS. 1, 2 and 3 are, respectively, an external view, plan view and side view of an illustrative embodiment of the sampling device according to the invention.

FIGS. 5A, 5B, 5C, 5D, 5E, 5F, 5G and 5H are views in longitudinal section of said device, showing the different steps in its functioning, namely:

Figure 4:
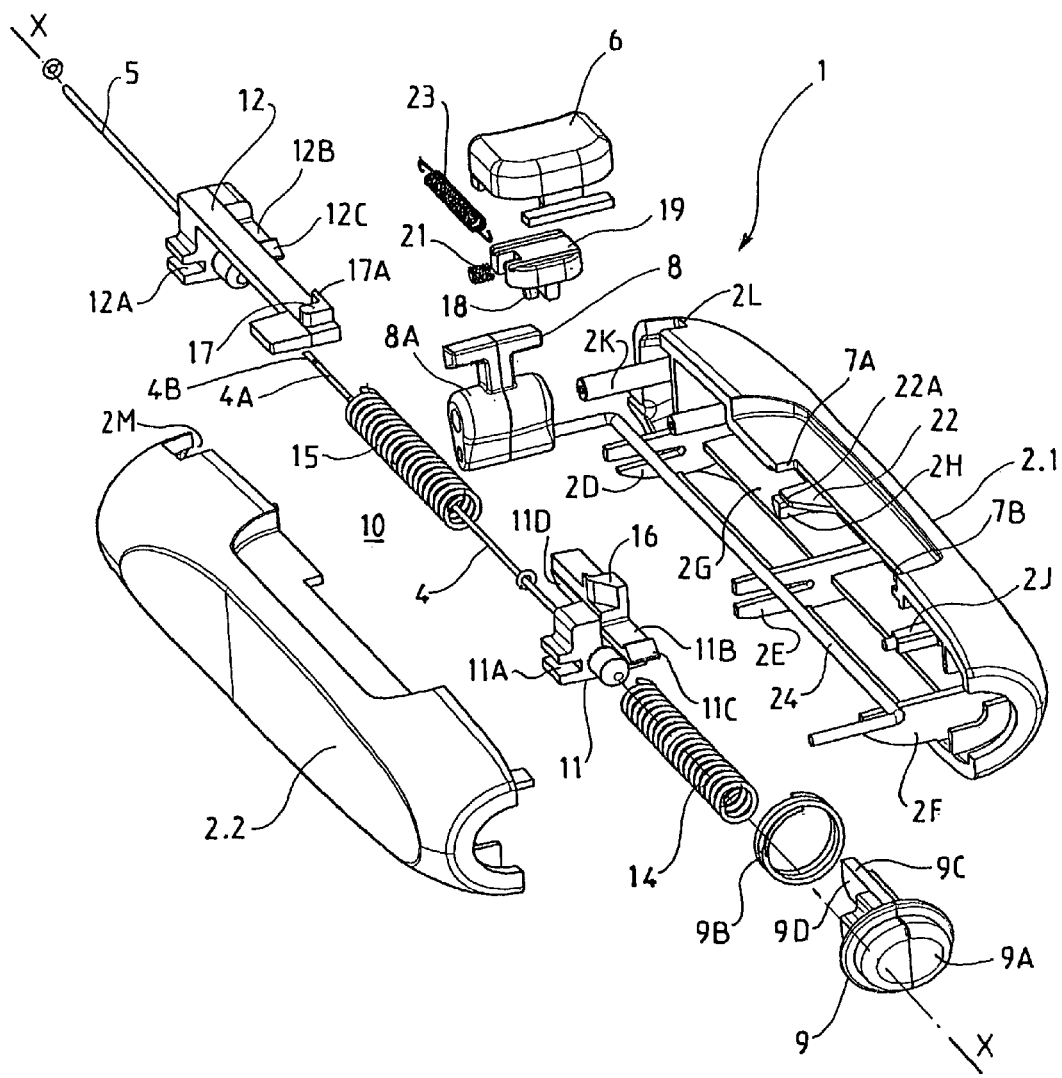
FIG. 4 is an exploded perspective view of said device, showing its different components.

slides with needle and cannula in the rest position;
first displacement of the control button for priming the slide with cannula;
return of the control button to the initial position;
second displacement of the control button for priming the slide with needle;
return of the control button to the initial position;
firing by the trigger mechanism and action on the means for blocking the slide with needle;
emergence of the slide with needle and action on the means for blocking the slide with cannula; and
emergence of the slide with cannula.

FIGS. 6A, 6B, 6C, 6D, 6E, 6F, 6G and 6H are sectional views along line I—I in FIGS. 5A, 5B, 5C, 5D, 5E, 5F, 5G and 5H, showing the different steps in the functioning of the control button of said device.

FIGS. 7A, 7B, 7C, 7D and 7E are perspective views, delimited by a rectangular frame, of said control button acting on the limit stops of the slides in the positions occupied by the device in FIGS. 5A through 5E respectively.

DETAILED DESCRIPTION OF THE INVENTION

The device 1 for taking a sample of body tissue, and shown in FIGS. 1 through 3, comprises a grippable housing 2 similar to a handle whose outer shape, being substantially parallelepipedal and rounded, is anatomical, allowing the practitioner to comfortably grip and easily use the device in one hand.

Protruding from the front face 2A of the housing are a needle 4, with a recess 4A, and a sampling cannula 5 coaxially surrounding the needle, except for the beveled insertion tip 4B, while a control button 6 is accessible from the top face 2B of the housing, via an opening 7 formed in the latter. These figures also show that the front tumbler 8 and the rear tumbler 9 of a trigger mechanism for firing said needle and cannula are accessible from the outside of the housing and are provided, respectively, on the top of the housing, near its front face 2A, and on its rear face 2C.

As is shown more particularly in FIG. 4, the grippable housing 2 is made up of two half-shells 2.1, 2.2 which are joined together to define a median longitudinal plane P—P of said housing, and an inner seat 10 inside which the various components of the sampling device 1 are mounted, which components will be described below with reference to FIGS. 4, 5A, 6A and 7A.

Provided inside the inner seat 10 of the housing 2 there are two slides 11, 12 which are arranged in series and support, respectively, the needle 4 and the cannula 5 on the same longitudinal axis X—X. In the embodiment illustrated, the slide 12 with cannula 5 is situated at the front of the housing 2, while the slide 11 with needle 4 is situated behind, that is to say directed toward the rear of the housing, its needle 4 extending through the cannula 5 and the associated slide 12 until its distal beveled tip 4B emerges from the cannula. Springs 14, 15 are also connected respectively to the slides by being arranged on the longitudinal axis X—X of the slides. Thus, the slide 12 with cannula is in abutment against a fixed front bracket 2D of the housing under the action of the spring 15 arranged between the slide and a fixed intermediate bracket 2E of the housing, and the slide 11 with needle is pressed against the fixed intermediate bracket 2E, on the other side, under the action of the spring 14 arranged between the slide and a third, fixed rear bracket 2F of the housing. These springs are of the compression type and are identical. These three brackets protrude, for example, from the half-shell 2.1 of the housing, transversely with respect to its longitudinal plane P—P.

Thus, under the action of these springs, said slides 11, 12 occupy a forward position in the housing 2, for which the needle 4 and cannula 5 are in an initial position of rest, not primed, and protruding substantially from the front face 2A of the housing.

Of course, the slides 11, 12 cooperate, in their displacement, with guides 2G issuing from the half-shells 2.1 and 2.2 and engage in respective lateral grooves 11A, 12A of these.

By means of a rearward displacement, parallel to the axis X—X, the control button 6 allows the slides 11, 12 to be brought to a rearward position, counter to the respective springs 14, 15, for which rearward position the needle 4 and cannula 5 are then in a retracted and primed position, ready for firing of the sampling device, as will be seen later with reference to FIG. 5D. Advantageously, in order to bring the slides to the rearward position sequentially, said slides are equipped with respective limit stops 16, 17 which are transversely offset with respect to one another, and the control button comprises a lug 18 which can be moved transversely, that is to say perpendicular to the plane P—P, under the action of displacement means and which can act sequentially on the limit stops.

Figure 6A:
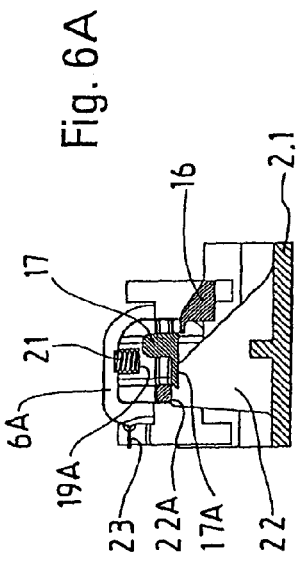
Figure 7A:
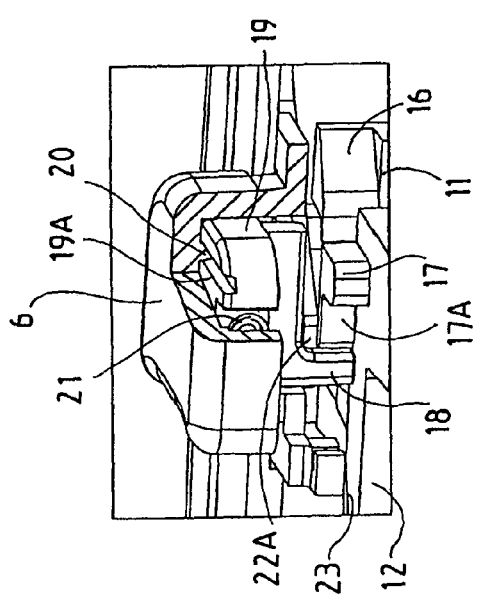
Figure 5A:
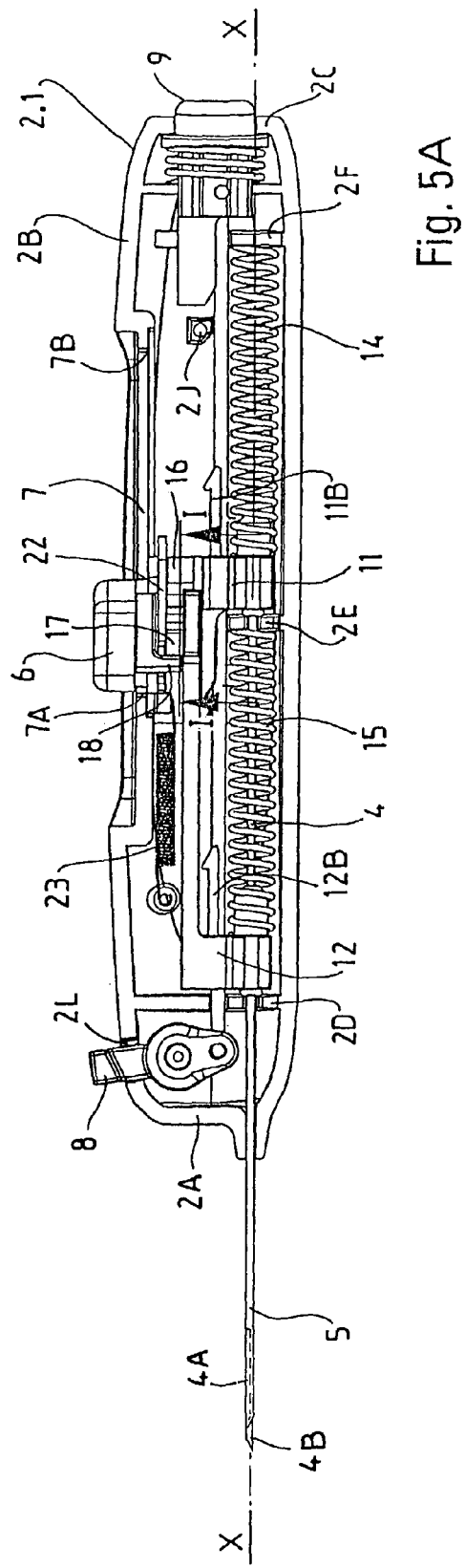

As is shown in FIGS. 4, 5A, 6A and 7A, the limit stop 17 is disposed vertically at the rear end of the slide 12 with cannula and is for example bent in an L-shape in which the movable lug 18 connected to the control button 6 can engage. Likewise, the other limit stop 16 is disposed vertically on the slide 11 with needle, being situated substantially at the same height as the limit stop 17 of the slide 12 (FIGS. 5A, 7A) but offset transversely from said limit stop 17 (FIGS. 6A, 7A). The limit stop 16 of the slide with needle is also bent for secure and reliable engagement of said lug 18. The latter projects vertically downward from said button 6 to reach just level with the slides, and it issues from a platform 19 accommodated inside the button and mounted so as to slide transversely in the latter via a slideway connection 20.

The means for displacement of the lug 18 advantageously comprise a spring 21 disposed transversely against a lateral wall 6A of the button and a recess 19A formed in the platform, and an inclined ramp 22 provided inside the housing and integral with the half-shell 2.1 from which it issues.

Thus, the spring 21 of the compression type ensures passage of the lug 18 from a retracted position, for which the slide 12 is displaced by its limit stop 17 toward its rearward position, to a deployed position for which the other slide 11 is displaced rearward via its limit stop 16 offset transversely with respect to that of the slide 12. And the ramp 22 returns said lug 18 to the retracted position, compressing the spring 21, upon return of the button 6 to the initial position.

It will be seen in particular from FIGS. 6A and 7A that the inclined ramp 22 terminates in an end edge 22A parallel to the axis X—X, on which edge the lug bears in the initial position of the button, and which edge is advantageously situated in the continuation of the corresponding side 17A of the L-shaped abutment 17.

It will also be noted that the control button 6 is maintained in the initial position by a draw spring 23 connecting it to the half-shell 2.1 of the housing and bringing it against the front edge 7A of the oblong opening 7 of said housing.

Moreover, the device 1 also comprises blocking means for immobilizing the slides 11, 12 when these occupy the rearward position. For this purpose, each slide 11, 12 comprises, in this illustrative embodiment, an elastically deformable longitudinal bracket 11B, 12B terminating in a hook 11C, 12C which is able to latch together with a corresponding fixed limit stop 2J, 2H protruding transversely from the half-shell 2.1 of the housing.

As regards the trigger mechanism, the front tumbler 8 and the rear tumbler 9 can be actuated independently of one another depending on the preference of the practitioner, while at the same time being advantageously connected mechanically to one another in order to act on the blocking means 11B, 11C, 2J–12B, 12C, 2H in the rearward position of the slides.

Structurally, the front tumbler 8 issues from a lever 8A mounted so as to pivot about an axle 2K situated in the front part of the half-shell and arranged orthogonally with respect to the axis X—X or to the longitudinal plane P—P of the housing 2. As regards the rear tumbler 9, it is of the type with a longitudinally displaceable pushbutton 9A, with a return spring 9B provided between it and the rear face 2C of the housing, and equipped with a bracket 9C projecting longitudinally into the inside of said housing. This bracket 9C is intended to come into contact with the blocking means 11B, 11C in order to cancel them and free the rear slide 11, which also comprises a longitudinal bracket 11D, opposite the bracket 11B, in order to act on the blocking means 12B, 12C of the slide 12 in the housing, as will be seen later.

The pivoting lever 8A of the front tumbler and the pushbutton 9A of the rear tumbler are connected by a rod 24 running through the inside of the housing and engaging via its ends in corresponding holes 8B, 9E provided in the lever 8A and the bracket 9C of the pushbutton. Thus, an action on either one of the tumblers causes displacement of the bracket 9C acting on the blocking means.

It will also be noted in FIGS. 2 and 3 that the front tumbler 8 is slightly offset transversely with respect to the longitudinal plane P—P of the housing 1. This transverse offset constitutes a safety means for the trigger mechanism, and the latter can be rendered active only if the practitioner brings it into the longitudinal plane P—P. To this end, this safety means is defined by a notch 2L transversely continuing the opening 2M formed in the top of the housing for the passage of the lever 8A of the front tumbler, which lever can slide transversely on its axle 2K in order to be brought into or out of the notch 2L by the practitioner. This front tumbler 8 (and thus the trigger mechanism) is rendered operative only if the practitioner displaces it transversely toward the longitudinal plane in the direction of arrow F3.

The way in which the sampling device 1 according to the invention works will now be described.

The device is initially in the configuration illustrated in FIGS. 1, 2, 5A, 6A and 7A, for which:

the slides 11, 12 occupy the forward position in the housing, abutting against the front and intermediate brackets 2B, 2E, respectively, under the action of the springs 14, 15, for which position the cannula 5 and needle 4 are in the initial protruding position of rest; the beveled tip of the cannula 5 covering the recess 4A of the needle;

the control button 6 is in the initial front position, under the action of the spring 23, against the front edge 7A of the opening of the housing 2;

the lug 18 is in contact with the lateral end edge 22A of the inclined ramp; and the trigger mechanism 8, 9 is inactive.

Figure 6B:
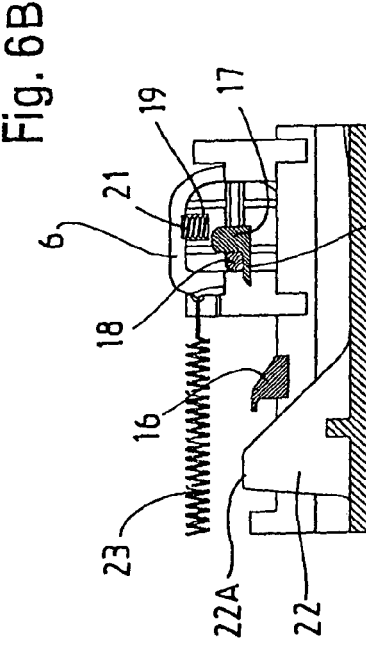
Figure 7B:
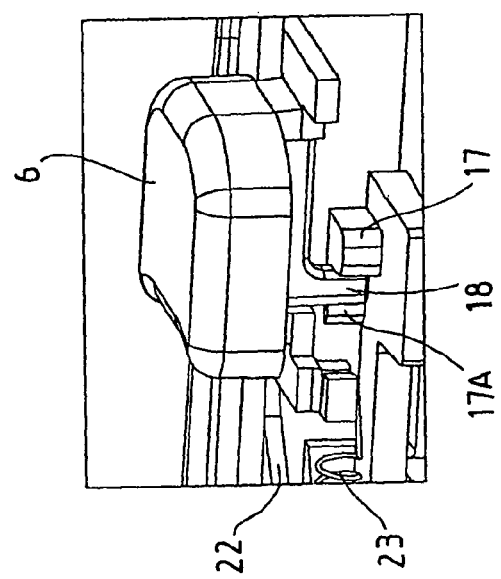
Figure 5B:
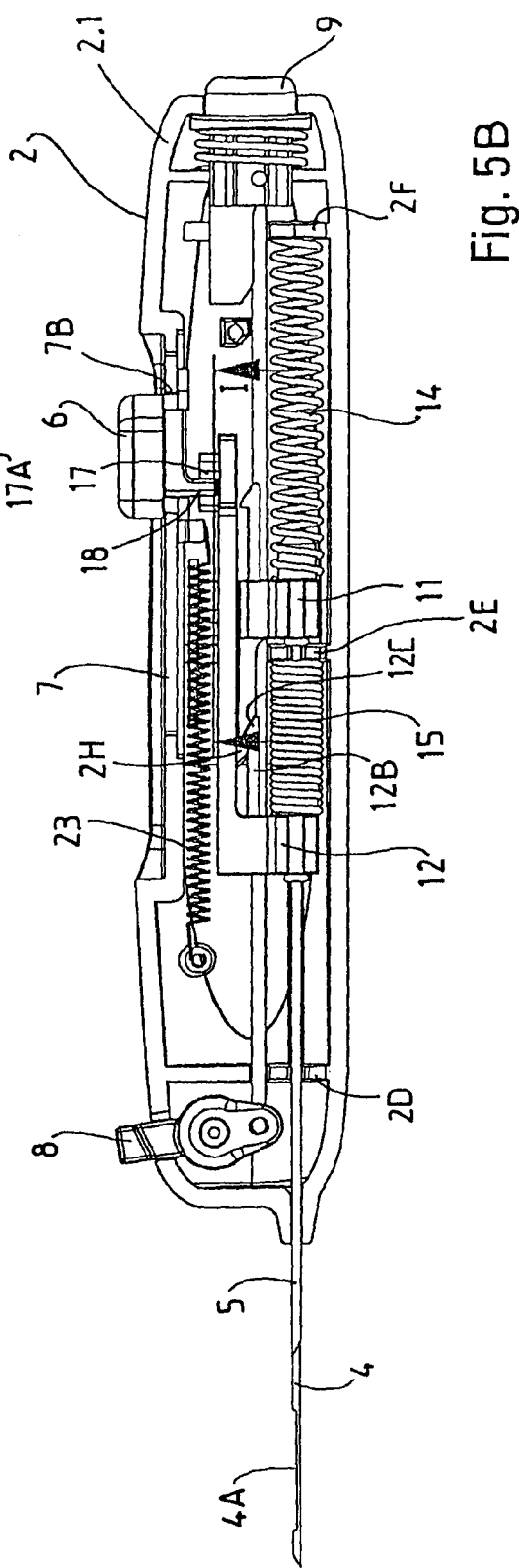

When the practitioner wishes to proceed with priming the device 1, he draws the control button 6 back using his thumb until said button comes into abutment against the rear edge 7B of the opening 7. As is shown in FIGS. 5B, 6B and 7B, as soon as the button starts to move longitudinally toward the rear, the lug 18 engages in the bent limit stop 17 of the slide 12, which is situated in the continuation of the end edge 22A of the ramp 22. The lug 18 remains in its initial transverse position with its spring compressed, since it bears against the side 17A of the limit stop. Thus, the slide 12 is entrained and moves from its forward position to its rearward position, compressing its spring 15, until the hook 12C of its elastically deformable bracket 12B engages with the corresponding limit stop 2H of the housing. The cannula 5, which has drawn back with its slide, is then in the primed position. The sampling recess 4A of the needle 4 is uncovered in FIG. 5B.

When the control button 6 returns from its rearward position to its forward position via its spring 23, as is shown in FIGS. 5C, 6C and 7C, the lug 18 escapes the limit stop 17 of the slide 12, so that it is displaced transversely in the deployed position by the action of the spring 21 which relaxes and displaces the platform 19 via the slideway 20. Then, when the lug touches the inclined ramp 22, it follows the latter and resumes its retracted position shown in FIGS. 5C, 6C and 7C, until it comes to the end edge 22A of the ramp, returning the platform 19 and thus compressing its associated spring 21. The button 6 then occupies its initial position under the action of its spring, against the front edge 7A.

After priming the cannula, the practitioner proceeds with the priming of the needle 4. To do this, as is shown in FIGS. 5D, 6D and 7D, he once again uses his thumb to draw the control button 6 back until it comes into abutment against the rear edge 7B of the opening, causing stretching of the spring 23. During this rearward longitudinal displacement of the button, as the slide 12 with cannula is in its rearward position, the lug 18 leaves the end edge 22A of the ramp, then follows its inclined edge by transverse displacement of its spring 21, causing its platform 19 to slide. By means of this transverse offset perpendicular to the plane P of the device, produced by the spring changing from its compressed state to its extended state, the lug 18 then engages in the bent limit stop 16 of the slide 11 with needle and thus entrains it to its rearward position. Once this position has been reached, the hook 11C of its elastically deformable longitudinal bracket 11B engages the corresponding limit stop 2J of the housing, so that the slide 11 is locked in its rearward position, the spring 14 being compressed and its needle 4 being primed in the cannula.

Figure 6E:
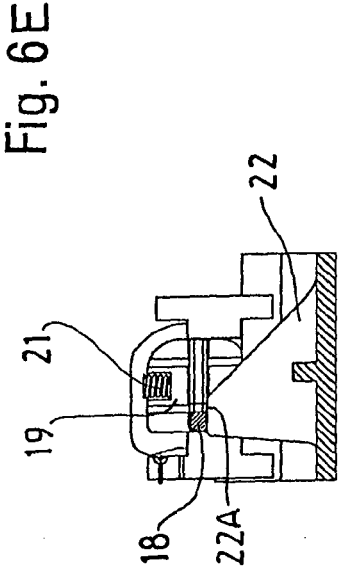
Figure 7E:
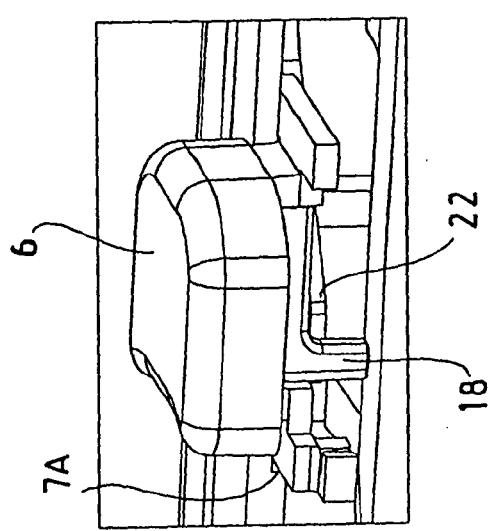
Figure 5E:
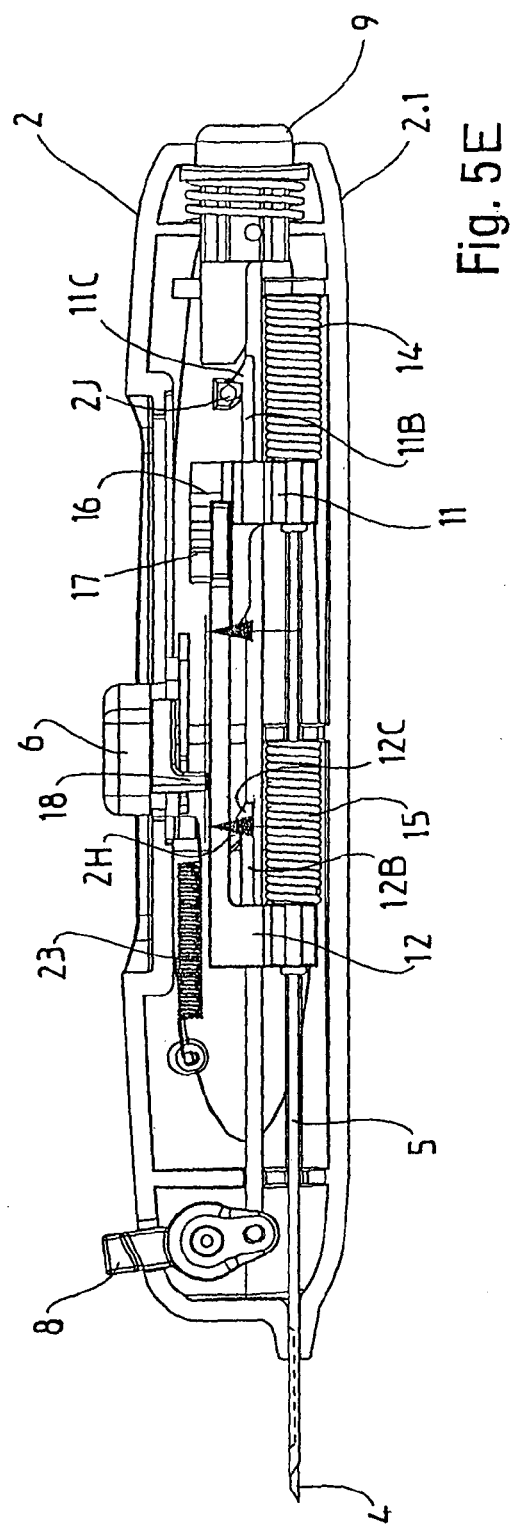

When the practitioner releases the button 6, the latter is brought elastically via the spring 23 to its initial position against the front edge 7A of the opening 7, and the lug 18 once again bears against the end edge 22A of the ramp 22, the spring compressing and pushing the platform 19 back. The device 1 is then in the primed position ready for sampling, as is shown in FIGS. 5E, 6E and 7E.

Thus, the device 1 is primed using just one hand and in a sequential manner involving two successive rearward displacements of the control button 6, which acts in the first instance on the slide 12 with cannula 5 and then acts secondly on the slide 11 with needle 4.

The practitioner can then proceed with firing the sampling device, as shown in FIGS. 5F, 5G and 5H.

Sampling can be triggered either with the front tumbler 8, by pivoting its lever 8A in the direction of arrow F1 in FIG. 5F about the axle 2K, or with the rear tumbler 9 by pushing the pushbutton 9A forward in the direction of arrow F2. Beforehand, however, the practitioner will have brought the front tumbler 8 into the longitudinal plane P—P and will have done this by acting on this front tumbler in the direction of arrow F3 in FIGS. 2 and 3, which causes the lever 8A to slide along its axle 2K and distances it from the notch 2L. The safety means is thus overridden and the trigger mechanism is rendered operational.

It will be seen in FIG. 5F that the end of the longitudinal bracket 9C of the pushbutton with inclined face 9D bears on the hook 11C of the elastic bracket 11B of the slide 11 until elastically deforming it and disengaging the hook 11C from the corresponding fixed limit stop 2J.

As is shown in FIG. 5G, the slide 11, under the action of the compressed spring 14, is displaced against the fixed intermediate bracket or limit stop 2E, which causes the needle to emerge and penetrate into the patient's body tissue (not shown). It will be seen from FIG. 6G that the limit stop 16 of the slide 11 has returned to its starting position near the lug 18. Just before the slide 11 with needle reaches its limit stop 2E, the front longitudinal bracket 11D of this slide bears against the hook 12C of the elastically deformable bracket 12B of the slide 12 with cannula and acts on the latter in order to disengage it from its limit stop 2H. As is shown in FIG. 5H, the effect of this is to cause the forward displacement of the slide 12 with cannula as far as the fixed front limit stop 2D, under the action of the compressed spring 15 which relaxes, and the protrusion of the cannula 5 into the body tissue, where it surrounds the needle in order to collect the tissue sample situated in the recess 4A of the needle 4. It will be seen from FIG. 6H that the limit stop 17 of the slide 12 has returned to the area of the end edge 22A of the ramp and of the lug 18.

Meanwhile, the tumblers 8, 9 resume their initial position under the action of the return spring 9B. The practitioner then withdraws the needle and cannula of the device 1 from the patient.

The invention claimed is:

1. A device for taking samples from a body, said device comprising:

a needle whose distal end forms a recess able to receive said sample;

a cannula coaxially surrounding said needle, said needle and cannula being able to slide relative to one another;

a first slide and a second slide connected respectively to said needle and cannula;

a first spring and a second spring connected respectively to said first and second slides;

a grippable housing of elongate shape, defining an inner seat inside which are arranged in series, on a longitudinal axis of said housing, said slides which are able to slide between a forward position in the housing, for which said needle and cannula are in a rest position and ready to be primed for taking a sample, and a rearward position for which said needle and cannula are in a primed, retracted position ready for said sampling;

a control button for bringing said slides to the rearward position counter to said respective springs;

a blocking device that blocks said slides in the rearward position; and a trigger mechanism for canceling said blocking device and, under the action of said springs, causing the forward displacement of said slides and firing of said needle and cannula, said trigger mechanism comprising, on said housing, a front tumbler and a rear tumbler, wherein:

said first and second slides comprise limit stops which are transversely offset with respect to one another, and said control button comprises a lug which can be moved transversely under the action of a displacement device and acts sequentially on said offset limit stops in order to bring said slides one after the other to the rearward position to provide sequential charging of the needle and cannula, said displacement device comprises a spring arranged transversely between said button and said lug and permitting the latter to pass from a retracted position, for which one of said slides is displaced to the rearward position via its limit stop, to a deployed position for which the other of said slides is displaced to the rearward position via its offset limit stop, and an inclined ramp which is provided inside said housing and which returns said lug from its deployed position to its retracted position, upon return of said button to the initial position, said second slide with cannula and its spring are situated at the front of said housing and are brought first to the rearward, primed position via said lug, while said first slide with needle and its spring are situated coaxially at the front of said housing and are displaced secondly to the rearward, primed position, the displacement of said slides and springs being limited by brackets fixed to said housing, and both the charged needle and cannula are automatically fired upon the actuation of either one of the front and rear tumblers.

2. The device as claimed in claim 1, wherein said inclined ramp terminates in a lateral end edge on which, in the initial position of said button, said lug bears, compressing its spring, and which is situated at the same level as the limit stop of the one slide to be displaced first.

3. The device as claimed in claim 1, wherein said lug is connected to said button by a slideway connection and can slide transversely, via the latter, under the action of the displacement device.

4. The device as claimed in claim 1, wherein said control button is mounted so as to slide longitudinally—relative to said housing—through an oblong opening of said housing, and wherein a spring arranged longitudinally—relative to said housing—connects said housing to said button in order to return the latter spontaneously to its initial position, against the corresponding front edge of said opening.

5. The device as claimed in claim 1, wherein said blocking device comprises at least one bracket with—an—elastically deformable hook issuing from each slide, and a corresponding fixed limit stop which is provided inside said housing and on which the hooked bracket of the corresponding slide engages when said slide arrives at the rearward position.

6. The device as claimed in claim 1, wherein said front and rear tumblers can be actuated independently of one another and act on said blocking device.

7. The device as claimed in claim 6, wherein said front and rear tumblers are connected mechanically to one another by a connection rod situated inside said housing.

8. The device as claimed in claim 6, wherein said rear tumbler comprises a pushbutton with return spring and equipped with a bracket arranged projecting into said housing in order to free said blocking device of said slide with needle, and wherein said slide with needle is equipped with an unblocking bracket arranged projecting in order to act on said blocking device of said slide with cannula, following its displacement to the forward position.

9. The device as claimed in claim 6, wherein said front tumbler comprises a lever pivoting about an axis of said housing orthogonal to its longitudinal axis, said connection rod connecting said lever of the front tumbler to said pushbutton of the rear tumbler.

10. The device as claimed in claim 6, further comprising a safety device that renders said trigger mechanism inoperative, said safety device having a notch which is formed in said housing and in which said front tumbler can be received following a transverse displacement.

11. The device as claimed in claim 1, wherein said housing comprises two half-shells joined together along the longitudinal plane.

* * * * *